United States Patent [19]

Eguchi et al.

[11] 3,979,392

[45] Sept. 7, 1976

[54] METHOD OF SEPARATING LIQUID DROPS FROM A GAS STREAM

[75] Inventors: Tomoki Eguchi; Kenji Akitsune; Michio Unoki; Jinichi Kataoka; Toshiki Kato; Atsuhiko Hiai, all of Takaishi, Japan

[73] Assignee: Mitsui Toatsu Chemicals, Incorporated, Tokyo, Japan

[22] Filed: Aug. 19, 1974

[21] Appl. No.: 498,719

[30] Foreign Application Priority Data

Aug. 22, 1973 Japan................................ 48-93284

[52] U.S. Cl....................... 260/249.7 A; 260/555 A
[51] Int. Cl.$^2$................ C07D 251/62; C07C 126/00
[58] Field of Search.................. 260/249.7 A, 555 R

[56] References Cited

UNITED STATES PATENTS

| 3,697,519 | 10/1972 | Kaasenbrood | 260/249.7 |
|---|---|---|---|
| 3,708,536 | 1/1973 | Hillenbrand | 260/249.7 |
| 3,723,430 | 3/1973 | Kokubo et al. | 260/249.7 |

*Primary Examiner*—John M. Ford
*Attorney, Agent, or Firm*—Fisher, Christen & Sabol

[57] ABSTRACT

Liquid drops such as molten urea contained in the waste gas from a melamine recovery process are separated from the waste gas by colliding the waste gas containing the liquid drops against a separator surface and providing said surface with a downwardly flowing film of a liquid such as molten urea.

6 Claims, No Drawings

METHOD OF SEPARATING LIQUID DROPS FROM A GAS STREAM

BACKGROUND OF THE INVENTION

1. Field of the Invention

The present invention relates to an improved method for separating drops of molten liquid, e.g., urea, contained in a gas stream discharged from a process wherein a melamine synthesis effluent gas containing melamine obtained from the thermal decomposition of urea or of thermal decomposition products of urea is cooled to separate melamine by crystallization, and the resulting effluent gas having melamine separated is closely contacted with a molten mass of, e.g., urea or a mixture of urea and thermal decomposition products thereof for recovering the unreacted urea and the like.

2. Description of the Prior Art

It is well known in the art that melamine is produced by heating urea or thermal decomposition products thereof with ammonia in the presence of a catalyst. There is also known a method for separating melamine, unreacted urea and thermal decomposition products of urea from the synthesis effluent gas containing melamine as disclosed in Japanese Patent Publication No. 21343/1966. This method comprises the steps of mixing the melamine synthesis effluent gas obtained by catalytically heating urea and the like with an inert gas thereby cooling the mixture to a temperature at which condensation of unreacted urea does not occur to selectively crystallize melamine so that only melamine is separated from the gas, closely contacting the effluent gas after the separation and still containing carbon dioxide, ammonia, melamine vapor and water vapor with molten urea or a molten mixture of urea and thermal decompositon products thereof maintained at a temperature above the melting point of urea to recover the unreacted urea and melamine vapor contained in the gas by dissolving or mixing them into said molten mass, and recirculating at least a portion of the gas stream from the recovery step as said inert gas for crystallization and separation of melamine.

In the above-described method, however, liquid drops composed of molten urea or of a molten mixture of urea and thermal decomposition products thereof that has been used for washing tend to be contained in the waste gas from the contacting step. Since this waste gas is mixed with the melamine synthesis effluent gas to cool the same, the aforementioned liquid drops are incorporated into the resultant crystallized melamine causing deterioration of the quality thereof. It is, therefore, necessary to remove said liquid drops prior to mixing of the waste gas with the melamine synthesis gas.

The separated liquid drops, however, adhere to the inner wall of the separator used and solidify thereon when the gas containing liquid drops is passed to a liquid-vapor separator for removing the liquid drops therefrom. This method has a disadvantage in the thus adhered mass which increases in amount with the passage of time, resulting in considerable lowering of the efficiency of the liquid-vapor separation and difficulties in continuous operation for an extended period of time. To overcome this disadvantage, it has been proposed in French Patent No. 1,560,175 to use a separator packed with Raschig rings and to flood the separator from time to time with molten urea to prevent formation of the solid incrustation. This method, however, has the disadvantage that it requires a plurality of liquid-vapor separators to be employed one at a time so that the installation cannot be operated continuously, thus rendering the operation considerably more complicated.

It is therefore an object of the present invention to provide a method of separating liquid urea drops from a waste gas from a washing step following melamine synthesis which ensures a continuous operation for an extended period of time and also facilitates the operation.

Still further objects and the entire scope of applicability of the present invention will become apparent from the detailed description given hereinafter; it should be understood, however, that the detailed description and specific example, while indicating preferred embodiments of the invention, are given by way of illustration only, since various changes and modifications within the spirit and scope of the invention will become apparent to those skilled in the art from this detailed description. It has been found that the above objects can be attained by practicing the present invention.

SUMMARY OF THE INVENTION

According to the present invention there is provided, in a method for separating liquid drops selected from the group consisting of urea, thermal decomposition products thereof and mixtures thereof with residual melamine contained in the waste gas from a melamine recovery process wherein a melamine synthesis effluent gas obtained by thermal decomposition of urea or the thermal decomposition products thereof is cooled to separate melamine therefrom by crystallization, and the remaining gas from which melamine has been separated is closely contacted with molten urea or a molten mixture (Molten mixture may contain solid melamine and/or solid thermal decomposition products of urea) of urea and the thermal decomposition products thereof to wash and recover unreacted urea, unreacted thermal decomposition products of urea and residual melamine contained in the gas, that improvement which comprises colliding the resultant waste gas containing said liquid drops against a separator surface and providing said surface with a downwardly flowing film of a liquid selected from the group consisting of molten urea, a molten mixture of urea and the thermal decomposition products of urea and molten mixtures thereof with melamine. This is accomplished by employing a separator of the type in which liquid drops are separated using centrifugal force and/or collision against a collection surface, e.g., the inner wall, of the separator.

Separators of the above-described type useful in the present invention for collecting liquid drops by their collision against a surface, e.g., the inner wall, of the separator and/or by centrifugal effect include cyclone separators, baffle plate type impingement separators, and lamellar separators comprising a plurality of surfaces that produce eddy currents on the collision plane. Suitable cyclone and impingement separators are disclosed in the Chemical Engineer's Handbook, John H. Perry, Ph.D., Editor, McGraw-Hill Book Company, Inc., 1950, and a suitable lamellar separator is that manufactured by Klöckner-Humbolt-Deutz AG of Germany and disclosed in German Patent No. 1,542,267.

For the formation of the downwardly flowing liquid film along the collection surface, e.g. inner surface, of the separator, any appropriate method may be employed, such as blowing the molten liquid onto the collection surface, e.g., the inner wall, of the separator, or a method in which the molten liquid is allowed to fall down along the collection surface due to the head difference of the liquid.

Liquids usable for the formation of the flowing liquid film along the collection surface of the separator may be a portion of the starting molten urea, the starting molten mixture of urea and thermal decomposition products thereof, or a molten liquid which is the same as that used for washing the synthesis effluent gas containing melamine. The molten liquid which has flowed down along the collection surface of the separator may be collected and reused for forming the liquid film, or may also be used as starting material or for washing the synthesis effluent gas. The molten liquid for formation of the downwardly flowing film may have added thereto, for lowering the melting point thereof, a compound soluble in the liquid such as ammonium salts of nitric acid, rhodanic acid, formic acid and acetic acid, or salts of guanidine with an acid, e.g., nitric acid, acetic acid, formic acid and rhodanic acid. Said compound may be used in an amount of from 10 to 90 % by weight of said molten liquid containing said compound.

In accordance with the present invention, it is now possible to avoid the situation in which a solid material adheres onto an inner surface of the separator thereby resulting in reduction of the separation efficiency thereof and, hence, in lowering of the quality of the melamine as well as in shortening the work period for continuously operating the installation. Thus, a continuous operation over a prolonged period of time has become possible.

The present invention will be described in more detail with reference to the following specific example wherein parts and percentages are by weight unless otherwise specified.

EXAMPLE

A melamine synthesis effluent gas maintained at 300°C. and flowing at a flow rate of 40 kg/hr. was mixed with a waste gas composed of 50% of ammonia and 50% of carbon dioxide and maintained at 140°C., which waste gas was derived from a contact stage thereof with molten urea, and the resultant mixture was cooled to 204°C. for crystallization to separate melamine crystals. The thus obtained waste gas was closely contacted with a molten mixture containing urea, biuret, cyanuric acid, and the like and maintained at 140°C. to cool the gas to 140°C. Urea and melamine and the like contained in the waste gas were absorbed into this molten mixture thereby increasing the melamine concentration of the molten liquid up to 2%. The waste gas contained 5 – 20 g/m$^3$ of liquid drops of the molten mixture. In order to separate the liquid drops, separation experiments were conducted using two kinds of separators, i.e., a cyclone separator and a lamellar separator, a separator composed of collision surfaces for the liquid drops and multiple surfaces which generate eddy currents. Operating conditions and the results of the experiments are shown in the following table, wherein the results are given in terms of time periods at the end of which the separation efficiencies were reduced down to 80% of the initial values.

Table

| Experiment Number | Separator Used | Downwardly flowing liquid film | Time period during which separation efficiency was maintained above 80% |
| --- | --- | --- | --- |
| 1. | Cyclone separator | None | 20 days |
| 2. | Cyclone separator | Formed along the inner surface of the separator by spraying 10 kg/hr of molten urea containing 1% of biuret | More than 150 days |
| 3. | Cyclone separator | A molten mixture of urea, melamine, and thermal decomposition products of urea used for cooling the waste gas, was flowed downwardly along the inner surface of the separator at the rate of 10 Kg/hr. | More than 150 days |
| 4. | Lamellar separator | None | 15 days |
| 5. | Lamellar separator | Same as that of Experiment No. 2. | More than 150 days |
| 6. | Lamellar separator | Same as that of Experiment No. 3. | More than 150 days |

As is apparent from the results shown in Experiments 2, 3, 5 and 6 in the table, the separation efficiency was maintained at a high level for a considerably prolonged period of time, irrespective of the type of the separator employed, when a downwardly flowing liquid film was formed along the inner surface of the separator, contrary to the results of Experiments 1 and 4 wherein the separation efficiency was lowered within a short period of time since no downwardly flowing liquid film was used.

What is claimed is:

1. In a method for separating liquid drops selected from the group consisting of urea, thermal decomposition products of urea, and mixtures thereof with residual melamine contained in the waste gas from a melamine recovery process wherein a melamine synthesis effluent gas obtained by thermal decomposition of urea or the thermal decomposition products thereof is mixed with waste gas whereby said effluent gas is cooled to separate melamine therefrom by crystallization, the remaining gas is washed with molten urea or a molten mixture of urea and the thermal decomposition products thereof to recover unreacted urea, unreacted thermal decomposition products of urea and residual melamine therefrom, and at least a portion of the resultant waste gas is separated from liquid drops contained therein and then recirculated for mixing with said effluent gas, the improvement which comprises colliding said resultant waste gas containing said liquid drops against a separator surface and providing said surface with a downwardly flowing film of a liquid selected from the group consisting of molten urea, a molten mixture of urea and the thermal decomposition products of urea and molten mixtures thereof with melamine, thereby separating said liquid drops from said waste gas without adherence of solidified liquid drops on said separator surface.

2. The method according to claim 1 wherein the separator used is selected from the group consisting of a cyclone separator, a baffle plate type impingement separator and a lamellar separator.

3. The method according to claim 1 wherein said liquid contains from 10 to 90 % by weight of a compound soluble therein for lowering the melting point of said liquid containing said compound.

4. The method according to claim 3 wherein said compound is selected from the group consisting of ammonium salts of nitric acid, rhodanic acid, formic acid and acetic acid and salts of quanidine with an acid.

5. The method according to claim 1 wherein said liquid is molten urea containing 1% by weight of biuret.

6. The method according to claim 1 wherein said liquid is a molten mixture of urea, melamine and the thermal decomposition products of urea.

* * * * *